United States Patent [19]

Arielly

[11] Patent Number: 5,334,703
[45] Date of Patent: Aug. 2, 1994

[54] CHROMOGENIC SUBSTRATE

[75] Inventor: Salo Arielly, Kungsbacka, Sweden

[73] Assignee: Chromonogenix AB, Molndal, Sweden

[21] Appl. No.: 859,717

[22] PCT Filed: Dec. 3, 1990

[86] PCT No.: PCT/SE90/00797
 § 371 Date: June 11, 1992
 § 102(e) Date: June 11, 1992

[87] PCT Pub. No.: WO91/09052
 PCT Pub. Date: June 27, 1991

[30] Foreign Application Priority Data

Dec. 12, 1989 [SE] Sweden .................................. 8904188

[51] Int. Cl.$^5$ ........................... C07K 5/00; C07K 5/10
[52] U.S. Cl. ........................................ 530/330; 435/23; 435/18
[58] Field of Search ..................... 530/330; 435/23, 18

[56] References Cited

U.S. PATENT DOCUMENTS

| 4,188,264 | 2/1980 | Iwanaga et al. | 23/230 B |
| 4,244,865 | 1/1981 | Ali et al. | 260/112.5 R |
| 4,279,810 | 7/1981 | Claeson et al. | 260/112.5 |
| 4,510,241 | 4/1985 | Mills | 435/23 |
| 4,563,305 | 1/1986 | Ryan et al. | 260/112.5 R |

FOREIGN PATENT DOCUMENTS

| 0080649 | 6/1983 | European Pat. Off. | G01N 33/50 |
| 0110306 | 6/1984 | European Pat. Off. | C07K 5/08 |
| 8202382 | 7/1982 | France | C07C 103/52 |
| 8200641 | 3/1982 | Sweden | C07C 103/52 |

Primary Examiner—Merrell C. Cashion, Jr.
Assistant Examiner—Carol A. Salata
Attorney, Agent, or Firm—Pollock, Vande Sande & Priddy

[57] ABSTRACT

The invention relates to, novel peptide derivatives with the formula: $R_1$-$A_1$-$A_2$-$A_3$-$A_4$-$R_2$ or its salt, wherein $R_1$=H or a protective group, $A_1$=H, Ile, Leu or Val, $A_2$=Glu, Asp, Ser, Thr; $A_3$=Gly or Glyc; $A_4$=Arg or Lys; $R_2$=4-nitroaniline with the proviso that $A_3$ is Gly when $A_4$ is Lys and that $A_3$ is Glyc when $A_4$ is Arg. The invention also discloses the process for the preparation of the peptide derivatives, the method for the determination of the bacterial endotoxins by the use of the invented peptide derivatives and the use of these derivatives for determination of bacterial endotoxins.

8 Claims, No Drawings

CHROMOGENIC SUBSTRATE

FIELD OF THE INVENTION

The present invention relates to a new chromogenic synthetic substrate used for quantitative determination of bacterial endotoxins in physiological fluids, food, pharmaceuticals etc.

THE BACKGROUND OF THE INVENTION

Bacterial endotoxins are produced by Gram negative bacteria and are considered by most investigators to be a very important factor in the development of septecemia. Several methods for determination of endotoxin have been described based on the observation by Levin and Bang (1956)that endotoxins specifically activate the clotting system of Limulus Potyphemus. In the beginning a test, in which Limulus Amebocyte Lysate (LAL)in contact with endotoxins containing sources, produce a specific gelation, had been developed. More recently chromogenic and fluorogenic methods based on the above observation have been developed and can rapidly detect small amounts of endotoxins (H. C. Hemker: Handbook of Synthetic Substrates, 1983, Martinus Nijhoff Publisher, Boston).

PRIOR ART

A. E. Torano et al have disclosed that an enzyme from Limulus amebocyte lysate shows similar specificity to mammalian blood coagulation factor $X_a$ (Thrombosis Research 34, 407–417, 1984), which recognize the sequence -Ile-Glu-Gly-Arg- in its natural substrate prothrombin.

Other investigations have also Shown the important role the COOH-terminal Gly-Arg sequence plays when analysing endotoxin. T. Harada et al, Biomedical Applications of the Horseshoe Crab (Limulidal), E. Cohen (ed), Alan R. Liss Inc. New York, 1979, pages 209–220, disclose in a table on page 213 different substrates which are used, but only those having the carboxy termial sequence Gly-Arg give interesting results. On page 212, lines 7-10 from the bottom, the authors point out: "These results clearly indicate that Limulus clotting enzyme displays a high specificity towards the peptide pNA having COOH-terminal Gly-Arg sequence".

U.S. Pat. Nos. 4,188,264 and 4,576,745 also give Gly-Arg as carboxy-terminal sequence in the substrate used for determination of endotoxin. Other substrates have been investigated, all of them showing Arg as carboxy terminal.

According to U.S. Pat. No. 4,406,832 the carboxy terminal should be -Ala-Arg- or -Cys-Arg-and this substrate has given relative activity which is as good as or a little better than standard -Gly-Arg-. Due to the complicated mechanism in these reactions it is not possible to know which peptide sequence could give an acceptable result.

Surprisingly and against the prior art within the field, we have now found that a substrate which has the carboxy terminal sequence -Gly-Lys- gives a relative activity which is at least 20% better compared with known substrates.

The use of Glycolic acid (Glyc) in a substrate for determination of endotoxin has never been disclosed before, and it is very surprising that the effect is as good when using -Glyc-Arg- as when using Gly-Lys, both of them giving a better effect than the normally used Gly-Arg.

DESCRIPTION OF THE INVENTION

The chromogenic synthetic peptide or peptide isostere derivative in the present invention shows high sensitivity in the method used for the determination of endotoxins.

The new substrates are characterized by the following formula:

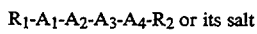

$R_1$-$A_1$-$A_2$-$A_3$-$A_4$-$R_2$ or its salt where
$R_1$=H or a protective group
$A_1$=H, Ile, Leu or Val
$A_2$=Glu, Asp, Ser, Thr
$A_3$=Gly or Glyc
$A_4$=Arg or Lys
$R_2$=4-nitro aniline with the proviso that $A_3$ is Gly when $A_4$ is Lys and that $A_3$ is Glyc when $A_4$ is Arg.

The present invention also discloses the process for the preparation of the peptid derivatives.

It also discloses the method for determination of bacterial endotoxins by the use of the derivative with the following formula:

$R_1$-$A_1$-$A_2$-$A_3$-$A_4$-$R_2$ or its salt where
$R_1$=H or a protective group
$A_1$=H, Ile, Leu or Val
$A_2$=Glu, Asp, Ser, Thr
$A_3$=Gly or Glyc
$A_4$=Arg or Lys
$R_2$=an aromatic or heterocyclic group which gives the compound
$R_2$-$NH_2$ by enzymatic hydrolysis
$R_2$-$NH_2$ are prior known compounds with chromogenic properties which permit quantifying of endotoxins by determination of splitted marker directly or after derivatization (H. C. Hemker: Loc. cit.)
with the proviso that $A_3$ is Gly when $A_4$ is Lys and that $A_3$ is Glyc when $A_4$ is Arg.

The use of these derivatives for determination of bacterial endotoxins is also disclosed.

Example of compounds which could be $R_2$-$NH_2$ are: p-nitroaniline, 3-carboxy-4-hydroxyaniline, 3-sulfo-4-nitroaniline, 3-alkoxy-4-nitroaniline, 3-carboxy-4-nitroaniline, 4-methyloxy-naphtylamine, 4-(N-ethyl-N-hydroxyethyl) aminoaniline, 5-amino-isophtalic acid-dimethyl ester, 5-amino-8-nitroquinoline, 7-amino-4-trifluormethyl coumarine, 7-amino-4-methyl coumarine, 4-aminodiphenylamine. The invention also discloses the use of these derivatives for determination of bacterial endotoxins.

The new peptide or peptide isostere derivatives contain as carboxyterminal Lys when combined with Gly and Arg when combined with Glyc. The combination Gly-Lys was considered unfavourable until present in substrates used for Limulus amebocyte lysate and the combination Glyc-Arg has never been used in this type of substrates before in methods for determination of bacterial endotoxins.

Description of Synthesis

| Abbreviations: | | | |
|---|---|---|---|
| Ac | = acetyl | Et₃N | = triethylamine |
| AcOH | = acetic acid | Glyc | = glycolic acid |
| AMC | = 7-amino-4-methylcoumarine | HOBT | = 1-hydroxybenzotriazol |
| Boc | = t-butyloxycarbonyl | HPLC | = high performance liquid chromatography |
| Bz | = benzoyl | | |
| Bzl | = benzyl | MeOH | = methanol |
| DCCI | = dicyclohexylcarbodiimide | ONp | = nitrophenyl ester |
| DCU | = dicyclohexylurea | OSu | = hydroxysuccinimide ester |
| DMAP | = dimethylaminopyridine | | |
| DMF | = dimethylformamide | pNA | = p-nitroaniline |
| EtOAc | = ethylacetate | TFA | = trifluoroacetic acid |
| EtOH | = ethanol | Z | = benzyloxycarbonyl |

Conventional techniques for coupling and conventional protecting groups (Z, Boc etc) used within the peptide chemistry (M. Bodanzsky: Principles of Peptide Synthesis, Springer Verlag 1984) e.g. addition step-by-step of the amino acids at the C-terminal amino acid provided with a marker or synthesis of the N-terminal peptide fragment per se, which then is coupled to the C-terminal amino acid provided with a marker, have been used.

The synthesis of different substrates according to the invention will be described more in detail in the following not limited working examples.

Purification of the intermediates and end products were performed by precipitation, crystallization or gel filtration chromatography. The purified end products were lyophilized. Prefabricated glass plates of silicagel $F_{254}$ were used for TLC analyses. After terminated chromatography the plates were inspected in U.V. light (254 nm) and were developed thereafter with ninhydrine and chlorine/dicarboxidine reagent. The Rf value given are results from single chromatographies.

Used solvent system for TLC have been indicated according to the following table:

| Indication | Solvent system | Volume ratio |
|---|---|---|
| A | n-butanol:AcOH:water | 3:2:1 |
| Pa₆ | chloroform:MeOH:AcOH:water | 34:4:9:2 |
| P1 | chloroform:MeOH | 9:1 |
| Pa | chloroform:MeOH:AcOH | 17:2:2 |

HPLC analysis were performed on Merck R. P. column (Hibar Lichracart) with 40% MeOH in 5% triethylaminophosphate pH 2.35 as eluent (1 ml/min). The optical activity of the end products were determined at 589 nm in 50% AcOH at a concentration of 0.4–1.0 g/100 ml at 25° C. The below mentioned abbreviations have the following meaning: (I.U.P.A.C. indication has been used were such exists).

| Amino acids: | |
|---|---|
| Arg = arginine | Val = valine |
| Gly = glycine | Glu = glutamic acid |
| Ile = isoleucine | Asp = aspartic acid |
| Leu = leucine | Ser = serine |
| | Thr = threonine |

All amine acids in the substrates have L-configurattion if not else is indicated.

The free amine acid or peptide is indicated by H- at the N-terminal amine group and —OH at the carboxy terminal group. The amine group is always given to the left and the carboxy to the right.

EXAMPLE 1

| | | |
|---|---|---|
| α-Ac—Ile—Glu—Gly—Lys—pNA.HCl | | molecular weight = 644.15 |
| 1a) | ε-Z—Lys—pNA.TFA | Molecular weight = 514.5 |

9 ml TFA is added to 10 mmol α-Boc-ε-Z-Lys-pNA dissolved in 25 ml methylenchloride. The solution is stirred for 30 minutes at room temperature and is precipitated with a mixture 2:1 of t-butylmethylether-petroleumether.

Yield 95%.

TLC: Rf=0.60 (A).

1b)   α-Boc-γ-O-Bzl-Glu-Gly-OH   Molecular weight=394.4

To 0.1 mol H-Gly-OH dissolved in 200 ml 1 molar NaHCO₃ a solution of 0.1 mol of α-Boc-γ-O-Bzl-Glu-O-Su in 200 ml dioxan is added. The mixture is stirred overnight at room temperature. Next day the solution is evaporated in vacuo to an oily residue which is dissolved in 100 ml water and washed with diethylether. The water phase is brought to pH 2 with KHSO₄ solution and extracted with EtOAc. After drying with Na₂SO₄, the EtOAc solution is evaporated and the substance precipitated with a mixture (1:1) of diethylether-petroleumether.

Yield 85%.

TLC: Rf=0.5 (Pa).

1c)   H-γ-O-Bzl-Glu-Gly-OH.TFA   Molecular weight=408.4

9 ml TFA is added to 10 mmol α-Boc-γ-O-Bzl-Glu-Gly-OH (1b) dissolved in 20 ml methylenchloride. The mixture is stirred for 30 minutes at room temperature, evaporated in vacuo to an oil and precipitated with diethylether.

Yield: 90%

TLC: Rf=0.44 (A).

1d)   α-Boc-Ile-γ-O-Bzl-Glu-Gly-OH   Molecular weight=507.6

To 0.1 mol H-γ-O-Bzl-Glu-Gly-OH.TFA dissolved in 250 ml 1 molar NaHCO₃ a solution of 0.1 mol α-Boc-Ile-O-Su in 250 ml dioxan is added. The mixture is stirred overnight at room temperature. Next day the solution is evaporated in vacuo, the residue dissolved in 100 ml water and washed with EtOAc. The water phase is brought to pH 3 with KHSO₄ solution and extracted with EtOAc. After drying with Na₂SO₄ the EtOAc solution is evaporated and the substance precipitated with petroleumether.

Yield: 92%

TLC: Rf=0.6 (Pa)

1e) α-Boc-Ile-γ-O-Bzl-Glu-Gly-ε-Z-Lys-pNA Molecular weight=890.0

3 mmol ε-Z-Lys-pNA.TFA (1a) dissolved in 25 ml DMF is neutralized in cold (−10° C.) with Et₃N. To the solution 3 mmol α-Boc-Ile-γ-O-Bzl-Glu-Gly-OH (1d), 3 mmol HOBT and 3.2 mmol DCCl are added. The mixture is stirred for 1 hour in cold and overnight at room temperature. The formed DCU is filtered off and the solution is evaporated in vacuo to an oil which is dissolved in EtOAc and is washed with 2% NaHCO₃, 2% KHSO₄ and H₂O. After drying with with Na₂SO₄, the EtOAc phase is evaporated and the substance is precipitated with diethylether.

Yield: 61%
TLC: Rf=0.67 (P₁)

1f) α-Ac-Ile-γ-O-Bzl-Glu-Gly-ε-Z-Lys-pNA Molecular weight=831.9

3.5 ml TFA is added to 1.2 mmol α-Boc-Ile-γ-O-Bzl-Glu-Gly-ε-Z-Lys-pNA (1e) in 6 ml methylenchloride. The mixture is stirred for 30 minutes at room temperature and is precipitated with diethyleter. The dry substance is dissolved in 10 ml DMF and neutralized in cold (−10° C.) with 160 μl Et₃N. 140 μl acetic anhydride is added and the mixture is stirred for 1 hour in cold and 2 hours at room temperature. The solution is evaporated in vacuo to an oil and the substance is precipitated with water.

Yield: 86%
TLC: Rf=0.45 (P1).

1) α-Ac-Ile-Glu-Gly-Lys-pNA.HCl Molecular weight=644.15

10 ml triflic acid is added to a cold (−10° C.) suspension of 1 mmol α-Ac-Ile-γ-O-Bzl-Glu-Gly-Z-Lys-pNA- (1f) in 10 ml methylenchloride. The mixture is stirred for 50 minutes at room temperature and precipitated with diethylether. The dried substance is ion exchanged on a Sephadex® QAE-25 column, in chloride form with 50% ETOH as eluent and is purified on a Merck Lobar® prepacked column (Lichroprep.® RP-8-B) with 50% MeOH as eluent (2 ml/minute). The purified product is lyophilized.

Yield: 42%
TLC: Rf=0.2 (Pa₆)
HPLC: 98% purity
$[\alpha]_D^{25} = -63.1°$ (C=0.5%)

EXAMPLE 2

α-Ac-Ile-Ser-Gly-Lys-pNA.HCl Molecular weight=602.11

2a) α-Boc-Gly-ε-Z-Lys-pNA Molecular weight=557.6

5 mmol ε-Z-Lys-pNA.TFA (prepared as described in example 1a) dissolved in 25 ml DMF is neutralized in cold (−10° C.) with Et₃N. To the solution 5 mmol α-Boc-Gly-OH, 5 mmol HOBT and 5 mmol DCCl are added. The mixture is stirred for 1 hour in cold and overnight at room temperature. The formed DCU is filtered off and the solution is evaporated in vacuo to an oil which is dissolved in EtOAc and washed with 2% NaHCO₃, 2% KHSO₄ and H₂O. After drying with Na₂SO₄ the EtOAc phase is evaporated in vacuo and the substance is precipitated with diethylether as an oil which solidifies in vacuo.

Yield: 73%
TLC: Rf=0.55 (P₁).

2b) α-Boc-O-Bzl-Ser-Gly-ε-Z-Lys,pNA Molecular weight=734.2

10 ml TFA is added to 5 mmol α-Boc-Gly-ε-Z-Lys-pNA (2a) dissolved in 20 ml methylenchloride. The mixture is stirred for 30 minutes at room temperature and the substance is precipitated with diethyleter. The dry substance is dissolved in 25 ml DMF and neutralized in cold (−10° C.) with Et₃N. To the solution 5 mmol α-Boc-O-Bzl-Ser-OH, 5 mmol HOBT and 5.1 mmol DCCl are added. The mixture is stirred for 1 hour in cold and overnight at room temperature. The formed DCU is filtered off and the solution is evaporated in vacuo to an oil which is dissolved in EtOAc and washed with 2% NaHCO₃, 2% KHSO₄ and H₂O. After drying with Na₂SO₄ the EtOAc phase is evaporated and the substance is precipitated with diethylether as an oil which solidifies in vacuo.

Yield: 86%
TLC: Rf=0.62 (P₁).

2c) α-Boc-Ile-O-Bzl-Ser-Gly-ε-Z-Lys-pNA Molecular weight:=848.0

10 ml TFA is added to 2 mmol α-Boc-O-Bzl-Ser-Gly-ε-Z-Lys-pNA (2b) dissolved in 20 ml methylenchloride. The mixture is stirred for 30 minutes at room temperature and the substance is precipitated with diethylether. The dry substance is dissolved in 25 ml DMF and neutralized in cold (−10° C.) with Et₃N. To the solution 2 mmol α-Boc-Ile-ONp is added. The mixture is stirred for 1 hour in cold and 48 hours at room temperature. The solution is evaporated in vacuo to an oil which is dissolved in EtOAc and washed with 2% NaHCO₃, 2% KHSO₄ and H₂O. After drying with Na₂SO₄ the EtOAc phase is evaporated and the substance is precipitated with diethylether.

Yield: 72%
TLC: Rf=0.62 (P₁).

2d) α-Ac-Ile-O-Bzl-Ser-Gly-ε-Z-Lys-pNA Molecular weight=789.9

5 ml TFA is added to 1 mmol α-Boc-Ile-O-Bzl-Ser-Gly-ε-Z-Lys-pNA (2c) dissolved in 10 ml methylenchloride. The mixture is stirred for 30 minutes at room temperature and the substance is precipitated with diethylether. The dry substance is dissolved in 10 ml DMF and neutralized in cold (−10° C.) with 80 μl Et₃N. 70 μl acetic anhydride is added ad the mixture is stirred for 1 hour in cold and 2 hours at room temperature. The solution is evaporated in vacuo to an oil and the substance is precipitated with water.

Yield: 85%
TLC: Rf=0.55 (P₁).

2) α-Ac-Ile-Ser-Gly-Lys-pNA.HCl Molecular weight=602.11

10 ml triflic acid is added to a cold (−10° C.) suspension of 1 mmol α-Ac-Ile-O-Bzl-Ser-Gly-ε-Z-Lys-pNA (2d) in 10 ml methylenchloride. The mixture is stirred for 50 minutes at room temperature and precipitated with diethylether. The product is ion exchanged and purified in the same way as in example 1.

Yield: 35%
TLC: Rf=0.2 (Pa₆)
HPLC: 97% purity.
$[\alpha]_D^{25} = -50.1°$ (c=0.5%)

EXAMPLE 3

α-Ac-Ile-Thr-Gly-Lys-pNA.HCl Molecular weight=616.13

3a) α-Boc-O-Bzl-Thr-Gly-ε-Lys-pNA Molecular weight=748.2

10 ml TFA is added to 5 mmol α-Boc-Gly-ε-Z-Lys-pNA (2a) dissolved in 20 ml methylenchloride. The mixture is stirred for 30 minutes at room temperature and the substance is precipitated with diethylether. The dry substance is dissolved in 25 ml DMF and neutralized in cold ($-10°$ C.) with Et$_3$N. To the solution 5 mmol α-Boc-O-Bzl-Thr-OH, 5 mmol HOBT and 5.1 mmol DCCl are added. The mixture is stirred for 1 hour in cold and overnight at room temperature. The formed DCU is filtered off and the solution is evaporated in vacuo to an oil, which is dissolved in EtOAc and washed with 2% NaHCO$_3$, 2% KHSO$_4$ and H$_2$O. After drying with Na$_2$SO$_4$ the EtOAc phase is evaporated and the substance is precipitated with diethylether as an oil which solidifies in vacuo.

Yield: 51%

TLC: Rf=0.65 (P$_1$).

3b) α-Boc-Ile-O-Bzl-Thr-Gly-ε-Z-Lys-pNA Molecular weight=862.0

10 ml TFA is added to 2 mmol α-Boc-O-Bzl-Thr-Gly-ε-Z-Lys-pNA (3a) dissolved in 20 ml methylenchloride. The mixture is stirred for 30 minutes at room temperature and the substance is precipitated with diethylether. The dry substance is dissolved in 25 ml DMF and neutralized in cold ($-10°$ C.) with Et$_3$N. To the solution 2 mmol α-Boc-Ile-ONp is added. The mixture is stirred for 1 hour in cold and 48 hours at room temperature. The solution is evaporated in vacuo to an oil which is dissolved in EtOAc and washed with 2% NaHCO$_3$, 2% KHSO$_4$ and H$_2$O. After drying with Na$_2$SO$_4$ the EtOAc phase is evaporated and the substance is precipitated with diethylether.

Yield: 50%

TLC: Rf=0.7 (P$_1$)

3c) α-Ac-Ile-O-Bzl-Thr-Gly-ε-Z-Lys-pNA Molecular weight=803.9

5 ml TFA is added to 1 mmol α-Boc-Ile-O-Bzl-Thr-Gly-ε-Z-Lys-pNA (3b) dissolved in 10 ml methylenchloride. The mixture is stirred for 30 minutes at room temperature and the substance is precipitated with diethylether. The dry substance is dissolved in 10 ml DMF and neutralized in cold ($-10°$ C.) with 80 μl Et$_3$N. 70 μl acetic anhydride is added and the mixture is stirred for 1 hour in cold ($-10°$ C.) and 2 hours at room temperature. The solution is evaporated in vacuo to an oil and the substance is precipitated in water.

Yield: 86%

TLC: Rf=0.55 (P$_1$)

3) Ac-Ile-Thr-Gly-Lys-pNA.HCl Molecular weight=616.13

10 ml triflic acid is added to a cold ($-10°$ C.) suspension of 1 mmol α-Ac-Ile-O-Bzl-Thr-Gly-ε-Z-Lys-pNA (3c) in 10 ml methylenchloride. The mixture is stirred for 50 minutes at room temperature and precipitated with diethylether. The product is ion exchanged and purified in the same way as in example 1.

Yield: 36%

TLC: Rf=0.21 (Pa$_6$)

HPLC: 97% purity $[α]_D^{25} = -53.2°$ (c=0.3%)

EXAMPLE 4

α-Ac-Ile-Glu-Gly-Arg-pNA.HCl Molecular weight=673.18

4a) Glyc-Arg-pNA.HCl Molecular weight:=388.8

5 mmol Arg-pNA.2 HBr dissolved in 30 ml DMF is neutralized in cold ($-10°$ C.) with Et$_3$N. To the solution 5 mmol glycolic acid, 5 mmol HOBT and 5.1 mmol DCCl are added. The mixture is stirred for 1 hour in cold and 72 hours at room temperature. The formed DCU is filtered off and the solution is evaporated in vacuo to an oil, which is purified on a Sephadex® QAE-25 column in chloride form with 90% ETOH as eluent.

Yield: 74%

TLC: Rf=0.35 (A).

4b) α-Boc-γ-O-Bzl-Glu-Glyc-Arg-pNA.HCl Molecular weight=708.2

To 5 mmol Glyc-Arg-pNA.HCl dissolved in 30 ml DMF and cooled to $-10°$ C., 5 mmol α-Boc-γ-O-Bzl-Glu-OH, 5 mmol HOBT, 0.5 mmol DMAP and 5.1 mmol DCCl are added. The mixture is stirred for 1 hour in cold and 48 hours at room temperature. The formed DCU is filtered off and the solution is evaporated in vacuo to an oil which is dissolved in EtOAc and washed with 2% NaHCO$_3$, 2% KHSO$_4$ and H$_2$O. After drying with Na$_2$SO$_4$, the EtOAc is evaporated and the substance is precipitated with diethylether.

Yield: 66%

TLC: Rf=0.35 (Pa$_6$).

4c) α-Boc-Ile-γ-O-Bzl-Glu-Glyc-Arg-pNA.HCl Molecular weight=821.3

10 ml TFA is added to 2 mmol α-Boc-γ-O-Bzl-Glu-Glyc-Arg-pNA.HCl (4b) dissolved in 20 ml methylenchloride. The mixture is stirred for 30 minutes at room temperature and the substance is precipitated with diethyleter. The dry substance is dissolved in 25 ml DMF and neutralized in cold ($-10°$ C.) with Et$_3$N. To the solution 2 mmol α-Boc-Ile-ONp is added. The mixture is stirred for 1 hour in cold and 48 hours at room temperature. The solution is evaporated in vacuo to an oil which is dissolved in EtOAc and washed with 2% NaHCO$_3$, 2% KHSO$_4$ and H$_2$O. After drying with Na$_2$SO$_4$ the EtOAc phase is evaporated and the substance is precipitated with diethylether.

Yield: 69%

TLC: Rf=0.43 (Pa$_6$)

4d) α-Ac-Ile-γ-O-Bzl-Glu-Glyc-Arg-pNA.HCl Molecular weight=763.3

5 ml TFA is added to 1 mmol α-Boc-Ile-γ-O-Bzl-Glu-Glyc-Arg-pNA.HCl (4c) dissolved in 10 ml methylenchloride. The mixture is stirred for 30 minutes at room temperature and the substance is precipitated with diethylether. The dried substance is dissolved in 10 ml DMF and neutralized in cold ($-10°$ C.) with 130 μl Et$_3$N. 120 μl acetic anhydride is added and the mixture is stirred for 1 hour in cold and 2 hours at room temperature. The solution is evaporated in vacuo to an oil and the substance is precipitated with H$_2$O.

Yield: 94%

TLC: Rf=0.34 (Pa$_6$).

4a-Ac-Ile-Glu-Glyc-Arg-pNA.HCl Molecular weight=673.18

10 ml triflic acid is added to a cold ($-10°$ C.) suspension of 1 mmol α-Ac-Ile-γ-O-Bzl-Glu-Glyc-Arg-pNA.HCl (4d) in 10 ml methylenchloride. The mixture is stirred for 50 minutes at room temperature and precipitated with diethylether. The substance is ion exchanged and purified in the same way as in example 1.

Yield: 31%

TLC: Rf=0.45 (A)

HPLC: 98% purity $[α]_D^{25} = -60.6°$ (c=0.4%)

Comparison of the Chromogenic Substrates Using a Single-stage Chromogenic LAL-test.*

*) Limulus Ameboecyte Lysate (H. C. Hemker Loc. cit.)

A series of endotoxin containing solutions, making up a standard curve in the range 0.1–1.2 EU/ml, were assayed as described below using the different chromogenic substrates. The slopes of the resulting standard curves were compared and the slope for the substrate S-2423 was considered to be 100%.

A reagent (100 μl) consisting of a mixture of LAL (50% of the clotting concentration) and the chromogenic substrate (4.4 mM) in a Tris buffer of pH 7.9 is added to an equal volume of the sample. The resulting reaction (activation of the LAL and the subsequent hydrolyses of the chromogenic substrate) is carried out at 37° C. After 15 min. the reaction is terminated by the addition of 400 μl of acetic acid and the absorbance is read at 405 nm.

Table I shows the results for the activated LAL with substrates as measured by the concentration of hydrolized pNA. Substrate S-2423 (Ac-Ile-Glu-Gly-Arg-pNA.HCl) is taken as standard.

TABLE I

Screening of substrate for single stage method - endotoxin with substrate concentration 2.2 mM (in the reaction solution). So = 2.2 mM

| Substrate | Peptide sequence | Relative activity |
|---|---|---|
| S-2423 | Ac—Ile—Glu—Gly—Arg—pNA.HCl | 100 |
| S-2834 | Ac—Ile—Glu—Gly—Lys—pNA.HCl | 126 |
| S-2854 | Ac—Ile—Ser—Gly—Lys—pNA.HCl | 131 |
| S-2860 | Ac—Ile—Glu-Glycolyl-Arg—pNA.HCl | 142 |

This table clearly shows that when using -Gly-Lys or Glyc-Arg as carboxy terminal sequence in the substrate, the activity is surprisingly considerably higher than when the known substrate S-2423, which has Gly-Arg as carboxyterminal sequence, is used.

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( i x ) FEATURE:
      ( A ) NAME/KEY: Peptide
      ( B ) LOCATION: 1..6
      ( D ) OTHER INFORMATION: /label=Page-2
         / note="chromogenic synthetic paptide or peptide isostere derivative"

( i x ) FEATURE:
      ( A ) NAME/KEY: Modified-site
      ( B ) LOCATION: 1
      ( D ) OTHER INFORMATION: /label=R1
         / note="H or a protective group"

( i x ) FEATURE:
      ( A ) NAME/KEY: Modified-site
      ( B ) LOCATION: 2
      ( D ) OTHER INFORMATION: /label=A1
         / note="H, Ile, Leu, or Val"

( i x ) FEATURE:
      ( A ) NAME/KEY: Modified-site
      ( B ) LOCATION: 3
      ( D ) OTHER INFORMATION: /label=A2
         / note="Glu, Asp, Ser, or Thr"

( i x ) FEATURE:
      ( A ) NAME/KEY: Modified-site
      ( B ) LOCATION: 4
      ( D ) OTHER INFORMATION: /label=A3
         / note="Gly or Glyc(glycolic acid)"

( i x ) FEATURE:
      ( A ) NAME/KEY: Modified-site
      ( B ) LOCATION: 5
      ( D ) OTHER INFORMATION: /label=A4
         / note="Arg or Lys"

( i x ) FEATURE:
      ( A ) NAME/KEY: Modified-site
      ( B ) LOCATION: 6
      ( D ) OTHER INFORMATION: /label=R2
         / note="4-nitro aniline"

( x i ) SEQUENCE DESCRIPTION: SEQ ID NO:1:

Xaa Xaa Xaa Xaa Xaa Xaa
1                  5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /label=Page-3
            / note="chromogenic synthetic peptide or peptide isostere derivative"

( i x ) FEATURE:
        ( A ) NAME/KEY: Modified-site
        ( B ) LOCATION: 1
        ( D ) OTHER INFORMATION: /label=R1
            / note="H or a protective group"

( i x ) FEATURE:
        ( A ) NAME/KEY: Modified-site
        ( B ) LOCATION: 2
        ( D ) OTHER INFORMATION: /label=A1
            / note="H, Ile, Leu, or Val"

( i x ) FEATURE:
        ( A ) NAME/KEY: Modified-site
        ( B ) LOCATION: 3
        ( D ) OTHER INFORMATION: /label=A2
            / note="Glu, Asp, Ser, or Thr"

( i x ) FEATURE:
        ( A ) NAME/KEY: Modified-site
        ( B ) LOCATION: 4
        ( D ) OTHER INFORMATION: /label=A3
            / note="Gly or Glyc(glycolic acid)"

( i x ) FEATURE:
        ( A ) NAME/KEY: Modified-site
        ( B ) LOCATION: 5
        ( D ) OTHER INFORMATION: /label=A4
            / note="Arg or Lys"

( i x ) FEATURE:
        ( A ) NAME/KEY: Modified-site
        ( B ) LOCATION: 6
        ( D ) OTHER INFORMATION: /label=R2
            / note="an aromatic or hetrerocyclic group which gives the compound R2-NH2 by enzymatice hydrolysis"

( x i ) SEQUENCE DESCRIPTION: SEQ ID NO:2:

Xaa Xaa Xaa Xaa Xaa Xaa
1                  5

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /label=Example-1

( i x ) FEATURE:
        ( A ) NAME/KEY: Modified-site

```
            ( B ) LOCATION: 1
            ( D ) OTHER INFORMATION: /note="alpha-acetyl"

( i x ) FEATURE:
            ( A ) NAME/KEY: Modified-site
            ( B ) LOCATION: 6
            ( D ) OTHER INFORMATION: /note="p-nitroaniline"

( i x ) FEATURE:
            ( A ) NAME/KEY: Modified-site
            ( B ) LOCATION: 7
            ( D ) OTHER INFORMATION: /note="trifluoroacetic acid"

( x i ) SEQUENCE DESCRIPTION: SEQ ID NO:3:

Xaa   Ile   Glu   Gly   Lys   Xaa   Xaa
  1                         5
```

( 2 ) INFORMATION FOR SEQ ID NO:4:

```
    ( i ) SEQUENCE CHARACTERISTICS:
            ( A ) LENGTH: 4 amino acids
            ( B ) TYPE: amino acid
            ( D ) TOPOLOGY: linear ( i i ) MOLECULE TYPE: peptide ( i x ) FEATURE:
            ( A ) NAME/KEY: Peptide
            ( B ) LOCATION: 1..4
            ( D ) OTHER INFORMATION: /label=Example-1a ( i x ) FEATURE:
            ( A ) NAME/KEY: Modified-site
            ( B ) LOCATION: 1
            ( D ) OTHER INFORMATION: /note="epsilon-benzyloxycarbonyl"

( i x ) FEATURE:
            ( A ) NAME/KEY: Modified-site
            ( B ) LOCATION: 3
            ( D ) OTHER INFORMATION: /note="p-nitroaniline"

( i x ) FEATURE:
            ( A ) NAME/KEY: Modified-site
            ( B ) LOCATION: 4
            ( D ) OTHER INFORMATION: /note="trifluoroacetic acid"

( x i ) SEQUENCE DESCRIPTION: SEQ ID NO:4:

Xaa   Lys   Xaa   Xaa
  1
```

( 2 ) INFORMATION FOR SEQ ID NO:5:

```
    ( i ) SEQUENCE CHARACTERISTICS:
            ( A ) LENGTH: 6 amino acids
            ( B ) TYPE: amino acid
            ( D ) TOPOLOGY: linear ( i i ) MOLECULE TYPE: peptide ( i x ) FEATURE:
            ( A ) NAME/KEY: Peptide
            ( B ) LOCATION: 1..5
            ( D ) OTHER INFORMATION: /label=Example-1b ( i x ) FEATURE:
            ( A ) NAME/KEY: Modified-site
            ( B ) LOCATION: 1
            ( D ) OTHER INFORMATION: /note="alpha-t-butyloxycarbonyl"

( i x ) FEATURE:
            ( A ) NAME/KEY: Modified-site
            ( B ) LOCATION: 2
            ( D ) OTHER INFORMATION: /note="gamma-Oxygen"

( i x ) FEATURE:
            ( A ) NAME/KEY: Modified-site
            ( B ) LOCATION: 3
            ( D ) OTHER INFORMATION: /note="benzyl"
```

( i x ) FEATURE:
     ( A ) NAME/KEY: Modified-site
     ( B ) LOCATION: 6
     ( D ) OTHER INFORMATION: /note="-OH group"

( x i ) SEQUENCE DESCRIPTION: SEQ ID NO:5:

Xaa Xaa Xaa Glu Gly Xaa
1               5

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /label=Example-1c ( i x ) FEATURE:
        ( A ) NAME/KEY: Modified-site
        ( B ) LOCATION: 1
        ( D ) OTHER INFORMATION: /note="Hydrogen"

( i x ) FEATURE:
        ( A ) NAME/KEY: Modified-site
        ( B ) LOCATION: 2
        ( D ) OTHER INFORMATION: /note="gamma-Oxygen"

( i x ) FEATURE:
        ( A ) NAME/KEY: Modified-site
        ( B ) LOCATION: 3
        ( D ) OTHER INFORMATION: /note="benzyl"

( i x ) FEATURE:
        ( A ) NAME/KEY: Modified-site
        ( B ) LOCATION: 6
        ( D ) OTHER INFORMATION: /note="-OH group"

( i x ) FEATURE:
        ( A ) NAME/KEY: Modified-site
        ( B ) LOCATION: 7
        ( D ) OTHER INFORMATION: /note="trifluoroacetic acid"

( x i ) SEQUENCE DESCRIPTION: SEQ ID NO:6:

Xaa Xaa Xaa Glu Gly Xaa Xaa
1               5

( 2 ) INFORMATION FOR SEQ ID NO:7:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /label=Example-1d ( i x ) FEATURE:
        ( A ) NAME/KEY: Modified-site
        ( B ) LOCATION: 1
        ( D ) OTHER INFORMATION: /note="alpha-t-butyloxycarbonyl"

( i x ) FEATURE:
        ( A ) NAME/KEY: Modified-site
        ( B ) LOCATION: 3
        ( D ) OTHER INFORMATION: /note="gamma-Oxygen"

( i x ) FEATURE:

( A ) NAME/KEY: Modified-site
( B ) LOCATION: 4
( D ) OTHER INFORMATION: /note="benx -continued ( D ) OTHER INFORMATION: /note="gamma-Oxygen"

( i x ) FEATURE:
                    ( A ) NAME/KEY: Modified-site
                    ( B ) LOCATION: 4
                    ( D ) OTHER INFORMATION: /note="benzyl"

( i x ) FEATURE:
                    ( A ) NAME/KEY: Modified-site
                    ( B ) LOCATION: 7
                    ( D ) OTHER INFORMATION: /note="epsilon-benzyloxycarbonyl"

( i x ) FEATURE:
                    ( A ) NAME/KEY: Modified-site
                    ( B ) LOCATION: 9
                    ( D ) OTHER INFORMATION: /note="p-nitroaniline"

( x i ) SEQUENCE DESCRIPTION: SEQ ID NO:9:

Xaa   Ile   Xaa   Xaa   Glu   Gly   Xaa   Lys   Xaa
    1                         5

( 2 ) INFORMATION FOR SEQ ID NO:10:

( i ) SEQUENCE CHARACTERISTICS:
                    ( A ) LENGTH: 7 amino acids
                    ( B ) TYPE: amino acid
                    ( D ) TOPOLOGY: linear ( i i ) MOLECULE TYPE: peptide ( i x ) FEATURE:
                    ( A ) NAME/KEY: Peptide
                    ( B ) LOCATION: 1..7
                    ( D ) OTHER INFORMATION: /label=Example-2

( i x ) FEATURE:
                    ( A ) NAME/KEY: Modified-site
                    ( B ) LOCATION: 1
                    ( D ) OTHER INFORMATION: /note="alpha-acetyl"

( i x ) FEATURE:
                    ( A ) NAME/KEY: Modified-site
                    ( B ) LOCATION: 6
                    ( D ) OTHER INFORMATION: /note="p-nitroaniline"

( i x ) FEATURE:
                    ( A ) NAME/KEY: Modified-site
                    ( B ) LOCATION: 7
                    ( D ) OTHER INFORMATION: /note="HCl"

( x i ) SEQUENCE DESCRIPTION: SEQ ID NO:10:

Xaa   Ile   Ser   Gly   Lys   Xaa   Xaa
    1                         5

( 2 ) INFORMATION FOR SEQ ID NO:11:

( i ) SEQUENCE CHARACTERISTICS:
                    ( A ) LENGTH: 5 amino acids
                    ( B ) TYPE: amino acid
                    ( D ) TOPOLOGY: linear ( i i ) MOLECULE TYPE: peptide ( i x ) FEATURE:
                    ( A ) NAME/KEY: Peptide
                    ( B ) LOCATION: 1..5
                    ( D ) OTHER INFORMATION: /label=Example-2a ( i x ) FEATURE:
                    ( A ) NAME/KEY: Modified-site
                    ( B ) LOCATION: 1
                    ( D ) OTHER INFORMATION: /note="alpha-t-butyloxycarbonyl"

( i x ) FEATURE:
                    ( A ) NAME/KEY: Modified-site
                    ( B ) LOCATION: 3
                    ( D ) OTHER INFORMATION: /note="epsilon-benzyloxycarbonyl"

( i x ) FEATURE:
    ( A ) NAME/KEY: Modified-site
    ( B ) LOCATION: 5
    ( D ) OTHER INFORMATION: /note="p-nitroaniline"

( x i ) SEQUENCE DESCRIPTION: SEQ ID NO:11:

Xaa Gly Xaa Lys Xaa
1               5

( 2 ) INFORMATION FOR SEQ ID NO:12:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=Example-2b ( i x ) FEATURE:
        ( A ) NAME/KEY: Modified-site
        ( B ) LOCATION: 1
        ( D ) OTHER INFORMATION: /note="alpha-t-butyloxycarbonyl"

( i x ) FEATURE:
        ( A ) NAME/KEY: Modified-site
        ( B ) LOCATION: 2
        ( D ) OTHER INFORMATION: /note="Oxygen"

( i x ) FEATURE:
        ( A ) NAME/KEY: Modified-site
        ( B ) LOCATION: 3
        ( D ) OTHER INFORMATION: /note="benzyl"

( i x ) FEATURE:
        ( A ) NAME/KEY: Modified-site
        ( B ) LOCATION: 6
        ( D ) OTHER INFORMATION: /note="epsilon-benzyloxycarbonyl"

( i x ) FEATURE:
        ( A ) NAME/KEY: Modified-site
        ( B ) LOCATION: 8
        ( D ) OTHER INFORMATION: /note="p-nitroaniline"

( x i ) SEQUENCE DESCRIPTION: SEQ ID NO:12:

Xaa Xaa Xaa Ser Gly Xaa Lys Xaa
1               5

( 2 ) INFORMATION FOR SEQ ID NO:13:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..9
        ( D ) OTHER INFORMATION: /label=Example-2c ( i x ) FEATURE:
        ( A ) NAME/KEY: Modified-site
        ( B ) LOCATION: 1
        ( D ) OTHER INFORMATION: /note="alpha-t-butyloxycarbonyl"

( i x ) FEATURE:
        ( A ) NAME/KEY: Modified-site
        ( B ) LOCATION: 3
        ( D ) OTHER INFORMATION: /note="Oxygen"

( i x ) FEATURE:
        ( A ) NAME/KEY: Modified-site (B) LOCATION: 4
(D) OTHER INFORMATION: /note="benzyl"

(ix) FEATURE:
(A) NAME/KEY: Modified-site
(B) LOCATION: 7
(D) OTHER INFORMATION: /note="epsilon-benzyloxycarbonyl"

(ix) FEATURE:
(A) NAME/KEY: Modified-site
(B) LOCATION: 9
(D) OTHER INFORMATION: /note="p-nitroaniline"

(xi) SEQUENCE DESCRIPTION: SEQ ID NO:13:

```
Xaa  Ile  Xaa  Xaa  Ser  Gly  Xaa  Lys  Xaa
 1                        5
```

(2) INFORMATION FOR SEQ ID NO:14:

(i) SEQUENCE CHARACTERISTICS:
(A) LENGTH: 9 amino acids
(B) TYPE: amino acid
(D) TOPOLOGY: linear (ii) MOLECULE TYPE: peptide (ix) FEATURE:
(A) NAME/KEY: Peptide
(B) LOCATION: 1..9
(D) OTHER INFORMATION: /label=Example-2d (ix) FEATURE:
(A) NAME/KEY: Modified-site
(B) LOCATION: 1
(D) OTHER INFORMATION: /note="alpha-acetyl"

(ix) FEATURE:
(A) NAME/KEY: Modified-site
(B) LOCATION: 3
(D) OTHER INFORMATION: /note="Oxygen"

(ix) FEATURE:
(A) NAME/KEY: Modified-site
(B) LOCATION: 4
(D) OTHER INFORMATION: /note="benzyl"

(ix) FEATURE:
(A) NAME/KEY: Modified-site
(B) LOCATION: 7
(D) OTHER INFORMATION: /note="epsilon-benzyloxycarbonyl"

(ix) FEATURE:
(A) NAME/KEY: Modified-site
(B) LOCATION: 9
(D) OTHER INFORMATION: /note="p-nitroaniline"

(xi) SEQUENCE DESCRIPTION: SEQ ID NO:14:

```
Xaa  Ile  Xaa  Xaa  Ser  Gly  Xaa  Lys  Xaa
 1                        5
```

(2) INFORMATION FOR SEQ ID NO:15:

(i) SEQUENCE CHARACTERISTICS:
(A) LENGTH: 7 amino acids
(B) TYPE: amino acid
(D) TOPOLOGY: linear (ii) MOLECULE TYPE: peptide (ix) FEATURE:
(A) NAME/KEY: Peptide
(B) LOCATION: 1..7
(D) OTHER INFORMATION: /label=Example-3

(ix) FEATURE:
(A) NAME/KEY: Modified-site
(B) LOCATION: 1
(D) OTHER INFORMATION: /note="alpha-acetyl"

( i x ) FEATURE:
    ( A ) NAME/KEY: Modified-site
    ( B ) LOCATION: 6
    ( D ) OTHER INFORMATION: /note="p-nitroaniline"

( i x ) FEATURE:
    ( A ) NAME/KEY: Modified-site
    ( B ) LOCATION: 7
    ( D ) OTHER INFORMATION: /note="HCl"

( x i ) SEQUENCE DESCRIPTION: SEQ ID NO:15:

Xaa  Ile  Thr  Gly  Lys  Xaa  Xaa
1                  5

( 2 ) INFORMATION FOR SEQ ID NO:16:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /label=Example-3a ( i x ) FEATURE:
        ( A ) NAME/KEY: Modified-site
        ( B ) LOCATION: 1
        ( D ) OTHER INFORMATION: /note="alpha-t-butyloxycarbonyl"

( i x ) FEATURE:
        ( A ) NAME/KEY: Modified-site
        ( B ) LOCATION: 2
        ( D ) OTHER INFORMATION: /note="Oxygen"

( i x ) FEATURE:
        ( A ) NAME/KEY: Modified-site
        ( B ) LOCATION: 3
        ( D ) OTHER INFORMATION: /note="benzyl"

( i x ) FEATURE:
        ( A ) NAME/KEY: Modified-site
        ( B ) LOCATION: 7
        ( D ) OTHER INFORMATION: /note="p-nitroaniline"

( x i ) SEQUENCE DESCRIPTION: SEQ ID NO:16:

Xaa  Xaa  Xaa  Thr  Gly  Lys  Xaa
1                  5

( 2 ) INFORMATION FOR SEQ ID NO:17:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..9
        ( D ) OTHER INFORMATION: /label=Example-3b ( i x ) FEATURE:
        ( A ) NAME/KEY: Modified-site
        ( B ) LOCATION: 1
        ( D ) OTHER INFORMATION: /note="alpha-t-butyloxycarbonyl"

( i x ) FEATURE:
        ( A ) NAME/KEY: Modified-site
        ( B ) LOCATION: 3
        ( D ) OTHER INFORMATION: /note="Oxygen"

( i x ) FEATURE:

(A) NAME/KEY: Modified-site
                (B) LOCATION: 4
                (D) OTHER INFORMATION: /note="benzyl"

(ix) FEATURE:
                (A) NAME/KEY: Modified-site
                (B) LOCATION: 7
                (D) OTHER INFORMATION: /note="epsilon-benzyloxycarbonyl"

(ix) FEATURE:
                (A) NAME/KEY: Modified-site
                (B) LOCATION: 9
                (D) OTHER INFORMATION: /note="p-nitroaniline"

(xi) SEQUENCE DESCRIPTION: SEQ ID NO:17:

Xaa  Ile  Xaa  Xaa  Thr  Gly  Xaa  Lys  Xaa
    1                        5

(2) INFORMATION FOR SEQ ID NO:18:

(i) SEQUENCE CHARACTERISTICS:
                (A) LENGTH: 9 amino acids
                (B) TYPE: amino acid
                (D) TOPOLOGY: linear (ii) MOLECULE TYPE: peptide (ix) FEATURE:
                (A) NAME/KEY: Peptide
                (B) LOCATION: 1..9
                (D) OTHER INFORMATION: /label=Example-3c (ix) FEATURE:
                (A) NAME/KEY: Modified-site
                (B) LOCATION: 1
                (D) OTHER INFORMATION: /note="alpha-acetyl"

(ix) FEATURE:
                (A) NAME/KEY: Modified-site
                (B) LOCATION: 3
                (D) OTHER INFORMATION: /note="Oxygen"

(ix) FEATURE:
                (A) NAME/KEY: Modified-site
                (B) LOCATION: 4
                (D) OTHER INFORMATION: /note="benzyl"

(ix) FEATURE:
                (A) NAME/KEY: Modified-site
                (B) LOCATION: 7
                (D) OTHER INFORMATION: /note="epsilon-benzyloxycarbonyl"

(ix) FEATURE:
                (A) NAME/KEY: Modified-site
                (B) LOCATION: 9
                (D) OTHER INFORMATION: /note="p-nitoraniline"

(xi) SEQUENCE DESCRIPTION: SEQ ID NO:18:

Xaa  Ile  Xaa  Xaa  Thr  Gly  Xaa  Lys  Xaa
    1                        5

(2) INFORMATION FOR SEQ ID NO:19:

(i) SEQUENCE CHARACTERISTICS:
                (A) LENGTH: 7 amino acids
                (B) TYPE: amino acid
                (D) TOPOLOGY: linear (ii) MOLECULE TYPE: peptide (ix) FEATURE:
                (A) NAME/KEY: Peptide
                (B) LOCATION: 1..7
                (D) OTHER INFORMATION: /label=Example-4

(ix) FEATURE:
                (A) NAME/KEY: Modified-site
                (B) LOCATION: 1

( D ) OTHER INFORMATION: /note="alpha-acetyl"

( i x ) FEATURE:
    ( A ) NAME/KEY: Modified-site
    ( B ) LOCATION: 4
    ( D ) OTHER INFORMATION: /note="glycolic acid"

( i x ) FEATURE:
    ( A ) NAME/KEY: Modified-site
    ( B ) LOCATION: 6
    ( D ) OTHER INFORMATION: /note="p-nitroaniline"

( i x ) FEATURE:
    ( A ) NAME/KEY: Modified-site
    ( B ) LOCATION: 7
    ( D ) OTHER INFORMATION: /note="HCl"

( x i ) SEQUENCE DESCRIPTION: SEQ ID NO:19:

Xaa Ile Glu Xaa Arg Xaa Xaa
1               5

( 2 ) INFORMATION FOR SEQ ID NO:20:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..4
        ( D ) OTHER INFORMATION: /label=Example-4a ( i x ) FEATURE:
        ( A ) NAME/KEY: Modified-site
        ( B ) LOCATION: 1
        ( D ) OTHER INFORMATION: /note="glycolic acid"

( i x ) FEATURE:
        ( A ) NAME/KEY: Modified-site
        ( B ) LOCATION: 3
        ( D ) OTHER INFORMATION: /note="p-nitroaniline"

( i x ) FEATURE:
        ( A ) NAME/KEY: Modified-site
        ( B ) LOCATION: 4
        ( D ) OTHER INFORMATION: /note="HCl"

( x i ) SEQUENCE DESCRIPTION: SEQ ID NO:20:

Xaa Arg Xaa Xaa
1

( 2 ) INFORMATION FOR SEQ ID NO:21:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=Example-4b ( i x ) FEATURE:
        ( A ) NAME/KEY: Modified-site
        ( B ) LOCATION: 1
        ( D ) OTHER INFORMATION: /note="alpha-t-butyloxycarbonyl"

( i x ) FEATURE:
        ( A ) NAME/KEY: Modified-site
        ( B ) LOCATION: 2
        ( D ) OTHER INFORMATION: /note="gamma-O"

( i x ) FEATURE:
    ( A ) NAME/KEY: Modified-site
    ( B ) LOCATION: 3
    ( D ) OTHER INFORMATION: /note="benzyl"

( i x ) FEATURE:
    ( A ) NAME/KEY: Modified-site
    ( B ) LOCATION: 5
    ( D ) OTHER INFORMATION: /note="glycolic acid"

( i x ) FEATURE:
    ( A ) NAME/KEY: Modified-site
    ( B ) LOCATION: 7
    ( D ) OTHER INFORMATION: /note="p-nitroaniline"

( i x ) FEATURE:
    ( A ) NAME/KEY: Modified-site
    ( B ) LOCATION: 8
    ( D ) OTHER INFORMATION: /note="HCl"

( x i ) SEQUENCE DESCRIPTION: SEQ ID NO:21:

Xaa Xaa Xaa Glu Xaa Arg Xaa Xaa
1               5

( 2 ) INFORMATION FOR SEQ ID NO:22:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..9
        ( D ) OTHER INFORMATION: /label=Example-4c ( i x ) FEATURE:
        ( A ) NAME/KEY: Modified-site
        ( B ) LOCATION: 1
        ( D ) OTHER INFORMATION: /note="alpha-t-butyloxycarbonyl"

( i x ) FEATURE:
        ( A ) NAME/KEY: Modified-site
        ( B ) LOCATION: 3
        ( D ) OTHER INFORMATION: /note="gamma-O"

( i x ) FEATURE:
        ( A ) NAME/KEY: Modified-site
        ( B ) LOCATION: 4
        ( D ) OTHER INFORMATION: /note="benzyl"

( i x ) FEATURE:
        ( A ) NAME/KEY: Modified-site
        ( B ) LOCATION: 6
        ( D ) OTHER INFORMATION: /note="glycolic acid"

( i x ) FEATURE:
        ( A ) NAME/KEY: Modified-site
        ( B ) LOCATION: 8
        ( D ) OTHER INFORMATION: /note="p-nitroaniline"

( i x ) FEATURE:
        ( A ) NAME/KEY: Modified-site
        ( B ) LOCATION: 9
        ( D ) OTHER INFORMATION: /note="HCl"

( x i ) SEQUENCE DESCRIPTION: SEQ ID NO:22:

Xaa Ile Xaa Xaa Glu Xaa Arg Xaa Xaa
1                   5

( 2 ) INFORMATION FOR SEQ ID NO:23:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
    ( A ) NAME/KEY: Peptide
    ( B ) LOCATION: 1..9
    ( D ) OTHER INFORMATION: /label=Example-4d ( i x ) FEATURE:
    ( A ) NAME/KEY: Modified-site
    ( B ) LOCATION: 1
    ( D ) OTHER INFORMATION: /note="alpha-acetyl"

( i x ) FEATURE:
    ( A ) NAME/KEY: Modified-site
    ( B ) LOCATION: 3
    ( D ) OTHER INFORMATION: /note="gamma-O"

( i x ) FEATURE:
    ( A ) NAME/KEY: Modified-site
    ( B ) LOCATION: 4
    ( D ) OTHER INFORMATION: /note="benzyl"

( i x ) FEATURE:
    ( A ) NAME/KEY: Modified-site
    ( B ) LOCATION: 6
    ( D ) OTHER INFORMATION: /note="glycolic acid"

( i x ) FEATURE:
    ( A ) NAME/KEY: Modified-site
    ( B ) LOCATION: 8
    ( D ) OTHER INFORMATION: /note="p-nitroaniline"

( i x ) FEATURE:
    ( A ) NAME/KEY: Modified-site
    ( B ) LOCATION: 9
    ( D ) OTHER INFORMATION: /note="HCl"

( x i ) SEQUENCE DESCRIPTION: SEQ ID NO:23:

Xaa Ile Xaa Xaa Glu Xaa Arg Xaa Xaa
1                      5

( 2 ) INFORMATION FOR SEQ ID NO:24:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /label=Table-1-seq-1

( i x ) FEATURE:
        ( A ) NAME/KEY: Modified-site
        ( B ) LOCATION: 1
        ( D ) OTHER INFORMATION: /note="acetyl"

( i x ) FEATURE:
        ( A ) NAME/KEY: Modified-site
        ( B ) LOCATION: 6
        ( D ) OTHER INFORMATION: /note="p-nitroaniline"

( i x ) FEATURE:
        ( A ) NAME/KEY: Modified-site
        ( B ) LOCATION: 7
        ( D ) OTHER INFORMATION: /note="HCl"

( x i ) SEQUENCE DESCRIPTION: SEQ ID NO:24:

Xaa Ile Glu Gly Arg Xaa Xaa
1                  5

( 2 ) INFORMATION FOR SEQ ID NO:25:

( i ) SEQUENCE CHARACTERISTICS:

(A) LENGTH: 6 amino acids
(B) TYPE: amino acid
(D) TOPOLOGY: linear (ii) MOLECULE TYPE: peptide (ix) FEATURE:
(A) NAME/KEY: Peptide
(B) LOCATION: 1..6
(D) OTHER INFORMATION: /label=Claim-16

(ix) FEATURE:
(A) NAME/KEY: Modified-site
(B) LOCATION: 1
(D) OTHER INFORMATION: /label=R1
/ note="H or a protective group"

(ix) FEATURE:
(A) NAME/KEY: Modified-site
(B) LOCATION: 2
(D) OTHER INFORMATION: /label=A1
/ note="H, Ile, Leu, or Val"

(ix) FEATURE:
(A) NAME/KEY: Modified-site
(B) LOCATION: 3
(D) OTHER INFORMATION: /label=A2
/ note="Glu, Asp, Ser, or Thr"

(ix) FEATURE:
(A) NAME/KEY: Modified-site
(B) LOCATION: 4
(D) OTHER INFORMATION: /label=A3
/ note="Gly or Glyc(glycolic acid)"

(ix) FEATURE:
(A) NAME/KEY: Modified-site
(B) LOCATION: 5
(D) OTHER INFORMATION: /label=A4
/ note="Arg or Lys"

(ix) FEATURE:
(A) NAME/KEY: Modified-site
(B) LOCATION: 6
(D) OTHER INFORMATION: /label=R2
/ note="a group that upon enzymatic hydrolysis
gives para- nitroaniline(pNA), with the proviso
that A3 is Gly when A4 is Lys and Glyc when A4 is (xi) SEQUENCE DESCRIPTION: SEQ ID NO:25:

Xaa Xaa Xaa Xaa Xaa Xaa
1               5

(2) INFORMATION FOR SEQ ID NO:26:

(i) SEQUENCE CHARACTERISTICS:
(A) LENGTH: 6 amino acids
(B) TYPE: amino acid
(D) TOPOLOGY: linear (ii) MOLECULE TYPE: peptide (ix) FEATURE:
(A) NAME/KEY: Peptide
(B) LOCATION: 1..6
(D) OTHER INFORMATION: /label=Claim-18a (ix) FEATURE:
(A) NAME/KEY: Modified-site
(B) LOCATION: 1
(D) OTHER INFORMATION: /note="alpha-acetal"

(ix) FEATURE:
(A) NAME/KEY: Modified-site
(B) LOCATION: 6
(D) OTHER INFORMATION: /note="p-nitroaniline"

(xi) SEQUENCE DESCRIPTION: SEQ ID NO:26:

Xaa Ile Glu Gly Lys Xaa ( 2 ) INFORMATION FOR SEQ ID NO:27:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 1..6
    ( D ) OTHER INFORMATION: /label=Claim-18b ( i x ) FEATURE:
    ( A ) NAME/KEY: Modified-site
    ( B ) LOCATION: 1
    ( D ) OTHER INFORMATION: /note="alpha-acetyl"

( i x ) FEATURE:
    ( A ) NAME/KEY: Modified-site
    ( B ) LOCATION: 6
    ( D ) OTHER INFORMATION: /note="p-nitroaniline"

( x i ) SEQUENCE DESCRIPTION: SEQ ID NO:27:

Xaa Ile Ser Gly Lys Xaa
  1         5

( 2 ) INFORMATION FOR SEQ ID NO:28:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 1..6
    ( D ) OTHER INFORMATION: /label=Claim-18c ( i x ) FEATURE:
    ( A ) NAME/KEY: Modified-site
    ( B ) LOCATION: 1
    ( D ) OTHER INFORMATION: /note="alpha-acetyl"

( i x ) FEATURE:
    ( A ) NAME/KEY: Modified-site
    ( B ) LOCATION: 6
    ( D ) OTHER INFORMATION: /note="p-nitroaniline"

( x i ) SEQUENCE DESCRIPTION: SEQ ID NO:28:

Xaa Ile Thr Gly Lys Xaa
  1         5

( 2 ) INFORMATION FOR SEQ ID NO:29:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 1..6
    ( D ) OTHER INFORMATION: /label=Claim-18d ( i x ) FEATURE:
    ( A ) NAME/KEY: Modified-site
    ( B ) LOCATION: 1
    ( D ) OTHER INFORMATION: /note="alpha-acetyl"

( i x ) FEATURE:
    ( A ) NAME/KEY: Modified-site
    ( B ) LOCATION: 4
    ( D ) OTHER INFORMATION: /note="Glyc(glycolic acid)"

( i x ) FEATURE:
    ( A ) NAME/KEY: Modified-site
    ( B ) LOCATION: 6
    ( D ) OTHER INFORMATION: /note="p-nitroaniline"

( x i ) SEQUENCE DESCRIPTION: SEQ ID NO:29:

```
Xaa  Ile  Glu  Xaa  Arg  Xaa
 1                  5
```

( 2 ) INFORMATION FOR SEQ ID NO:30:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /label=Claim-19

( i x ) FEATURE:
        ( A ) NAME/KEY: Modified-site
        ( B ) LOCATION: 1
        ( D ) OTHER INFORMATION: /label=R1
            / note="H or a protective group"

( i x ) FEATURE:
        ( A ) NAME/KEY: Modified-site
        ( B ) LOCATION: 2
        ( D ) OTHER INFORMATION: /label=A1
            / note="H, Ile, Leu, or Val"

( i x ) FEATURE:
        ( A ) NAME/KEY: Modified-site
        ( B ) LOCATION: 3
        ( D ) OTHER INFORMATION: /label=A2
            / note="Glu, Asp, Ser, or Thr"

( i x ) FEATURE:
        ( A ) NAME/KEY: Modified-site
        ( B ) LOCATION: 4
        ( D ) OTHER INFORMATION: /label=A3
            / note="Gly or Glyc(glycolic acid)"

( i x ) FEATURE:
        ( A ) NAME/KEY: Modified-site
        ( B ) LOCATION: 5
        ( D ) OTHER INFORMATION: /label=A4
            / note="Arg or Lys"

( i x ) FEATURE:
        ( A ) NAME/KEY: Modified-site
        ( B ) LOCATION: 6
        ( D ) OTHER INFORMATION: /label=R2
            / note="An aromatic or heterocyclic group which by
            enzymatic hydrolysis gives a compound R2-NH2 which
            can be determined quantitatively with the proviso ( x i ) SEQUENCE DESCRIPTION: SEQ ID NO:30:

```
Xaa  Xaa  Xaa  Xaa  Xaa  Xaa
 1                  5
```

( 2 ) INFORMATION FOR SEQ ID NO:31:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
    ( A ) NAME/KEY: Peptide
    ( B ) LOCATION: 1..6
    ( D ) OTHER INFORMATION: /label=Claim-21a ( i x ) FEATURE:
    ( A ) NAME/KEY: Modified-site
    ( B ) LOCATION: 1
    ( D ) OTHER INFORMATION: /note="alpha-acetyl"

( i x ) FEATURE:
    ( A ) NAME/KEY: Modified-site
    ( B ) LOCATION: 6
    ( D ) OTHER INFORMATION: /note="p-nitroaniline"

( x i ) SEQUENCE DESCRIPTION: SEQ ID NO:31:

Xaa Ile Glu Gly Lys Xaa
1                 5

( 2 ) INFORMATION FOR SEQ ID NO:32:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /label=Claim-21b ( i x ) FEATURE:
        ( A ) NAME/KEY: Modified-site
        ( B ) LOCATION: 1
        ( D ) OTHER INFORMATION: /note="alpha-acetyl"

( i x ) FEATURE:
        ( A ) NAME/KEY: Modified-site
        ( B ) LOCATION: 6
        ( D ) OTHER INFORMATION: /note="p-nitroaniline"

( x i ) SEQUENCE DESCRIPTION: SEQ ID NO:32:

Xaa Ile Ser Gly Lys Xaa
1                 5

( 2 ) INFORMATION FOR SEQ ID NO:33:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /label=Claim-21c ( i x ) FEATURE:
        ( A ) NAME/KEY: Modified-site
        ( B ) LOCATION: 1
        ( D ) OTHER INFORMATION: /note="aplha-acetyl"

( i x ) FEATURE:
        ( A ) NAME/KEY: Modified-site
        ( B ) LOCATION: 6
        ( D ) OTHER INFORMATION: /note="p-nitroaniline"

( x i ) SEQUENCE DESCRIPTION: SEQ ID NO:33:

Xaa Ile Thr Gly Lys Xaa
1                 5

(2) INFORMATION FOR SEQ ID NO:34:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /label=Claim-21d (ix) FEATURE:
        (A) NAME/KEY: Modified-site
        (B) LOCATION: 1
        (D) OTHER INFORMATION: /note="alpha-acetyl"

(ix) FEATURE:
        (A) NAME/KEY: Modified-site
        (B) LOCATION: 4
        (D) OTHER INFORMATION: /note="Glyc(glycolic acid)"

(ix) FEATURE:
        (A) NAME/KEY: Modified-site
        (B) LOCATION: 6
        (D) OTHER INFORMATION: /note="p-nitroaniline"

(xi) SEQUENCE DESCRIPTION: SEQ ID NO:34:

Xaa  Ile  Glu  Xaa  Arg  Xaa
    1                      5

I claim:

1. Peptide derivatives having the general formula:

$$R_1-A_1-A_2-A_3-A_4-R_2 \text{ or its salt}$$

wherein
$R_1$ = H or a protective group
$A_1$ = H, Ile, Leu or Val
$A_2$ = Glu, Asp, Ser, or Thr
$A_3$ = Gly or Glyc
$A_4$ = Arg or Lys
$R_2$ = is a group that upon enzymatic hydrolysis gives para-nitroaniline (pNA),
with the proviso that $A_3$ is Gly when $A_4$ is Lys and Glyc when $A_4$ is Arg.

2. Peptide derivatives according to claim 1 wherein $A_1$ = Ile.

3. Peptide derivatives according to claim 1 having the formula selected from the group consisting of:
α-Ac-Ile-Glu-Gly-Lys-pNA,
α-Ac-Ile-Ser-Gly-Lys-pNA,
α-Ac-Ile-Thr-Gly-Lys-pNA, and
α-Ac-Ile-Glu-Glyc-Arg-pNA.

4. A method for quantitatively determining bacterial endotoxins in a sample which comprises incubating the sample with a Limulus clotting enzyme and a substrate for said enzyme, wherein said substrate is a peptide derivative having the following formula:

$$R_1-A_1-A_2-A_3-A_4-R_2 \text{ or its salt}$$

where
$R_1$ = H or a protective group
$R_1$ = H, Ile, Leu or Val
$A_2$ = Glu, Asp, Ser, or Thr
$A_3$ = Gly or Glyc
$A_4$ = Arg or Lys
$R_2$ = an aromatic or heterocyclic group which by enzymatic hydrolysis gives a compound $R_2$-$NH_2$ which can be determined quantitatively,
with the proviso that $A_3$ is Gly when $A_4$ is Lys and Glyc when $A_4$ is Arg.

5. The method of claim 4 when A is Ile.

6. The method of claim 5 wherein said peptide derivative is selected from the group consisting of:
α-Ac-Ile-Glu-Gly-Lys-pNA,
α-Ac-Ile-Ser-Gly-Lys-pNA,
α-Ac-Ile-Thr-Gly-Lys-pNA, and
α-Ac-Ile-Glu-Glyc-Arg-pNA.

7. The method of claim 4 wherein said clotting enzyme is Limulus Amebocyte Lysate.

8. The method of claim 4 wherein $R_2$-$NH_2$ is para-nitroaniline.

* * * * *

UNITED STATES PATENT AND TRADEMARK OFFICE
CERTIFICATE OF CORRECTION

PATENT NO. : 5,334,703
DATED : August 2, 1994
INVENTOR(S) : Arielly

It is certified that error appears in the above-indentified patent and that said Letters Patent is hereby corrected as shown below:

```
Column  3, line 65, change "amine" to ---amino---.
Column  3, line 67, change "amine" to ---amino---.
Column  3, line 68, change "amine" to ---amino---.
Column  7, line 61, change "Gly" to ---Glyc---.
Column  8, line 53, change "4" to ---4)---.
Column 43, line 47, before "Glyc" insert ---that A_3 is---.
Column 44, line 45, before "Glyc" insert ---that A_3 is---.
```

Signed and Sealed this

Fourth Day of April, 1995

Attest:

BRUCE LEHMAN

Attesting Officer

Commissioner of Patents and Trademarks